US007947942B2

(12) United States Patent
Ouchi

(10) Patent No.: US 7,947,942 B2
(45) Date of Patent: *May 24, 2011

(54) PHOTOCONDUCTIVE ELEMENT AND SENSOR DEVICE

(75) Inventor: Toshihiko Ouchi, Sagamihara (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 12/612,798

(22) Filed: Nov. 5, 2009

(65) Prior Publication Data

US 2010/0051811 A1  Mar. 4, 2010

Related U.S. Application Data

(62) Division of application No. 11/683,782, filed on Mar. 8, 2007, now Pat. No. 7,633,043.

(30) Foreign Application Priority Data

Mar. 17, 2006  (JP) .................................. 2006-073613
Dec. 20, 2006  (JP) .................................. 2006-342883

(51) Int. Cl.
*G01N 21/01* (2006.01)
*H01S 1/02* (2006.01)
*H01S 5/12* (2006.01)
(52) U.S. Cl. ........... 250/214.1; 250/338.4; 257/E31.093
(58) Field of Classification Search ............... 250/214.1, 250/338.4; 343/700 MS; 257/E31.093; 438/22, 438/98, 459
See application file for complete search history.

(56) References Cited

U.S. PATENT DOCUMENTS 5,701,325 A  12/1997  Ouchi et al. ..................... 372/96
5,789,750 A  8/1998  Nuss .......................... 250/338.1
(Continued)

FOREIGN PATENT DOCUMENTS

JP  10-104171  4/1998

OTHER PUBLICATIONS

Y.C. Shen et al., "Generation and Detection of Ultrabroadband Terahertz Radiation Using Phoconductive Emitters and Receivers," Applied Physics Letters, vol. 85, No. 2, pp. 164-166, Jul. 12, 2004.

*Primary Examiner* — John R Lee
(74) *Attorney, Agent, or Firm* — Fitzpatrick, Cella, Harper & Scinto

(57) ABSTRACT

There is provided a photoconductive element capable of generating and detecting broadband electromagnetic waves such as terahertz waves at a comparatively high efficiency by decreasing or avoiding the absorption of electromagnetic waves into a substrate. A photoconductive element 1 includes a photoconductive film 5 exhibiting conductivity by the radiation of light, a substrate 6 holding the photoconductive film and a thin film sandwiched between the photoconductive film 5 and the substrate 6, the thin film being different in composition from the photoconductive film 5 and the substrate 6. The photoconductive film 5 is provided with an antenna 7 having a gap portion 2 and an electrode 4 electrically connectable to the antenna 7. At least a part of the photoconductive film where the gap portion 2 of the antenna 7 is located is single crystal. The substrate 6 has an opening portion 3 at a part corresponding to a part of the photoconductive film 5 where the gap portion 2 of the antenna 7 is located.

3 Claims, 7 Drawing Sheets

U.S. PATENT DOCUMENTS

| | | | |
|---|---|---|---|
| 5,850,408 A | 12/1998 | Ouchi et al. | 372/27 |
| 6,046,096 A | 4/2000 | Ouchi | 438/510 |
| 6,055,251 A | 4/2000 | Ouchi et al. | 372/28 |
| 6,089,442 A | 7/2000 | Ouchi et al. | 228/180.1 |
| 6,222,868 B1 | 4/2001 | Ouchi et al. | 372/50 |
| 6,320,691 B1 | 11/2001 | Ouchi et al. | 359/237 |
| 6,477,286 B1 | 11/2002 | Ouchi | 385/14 |
| 6,507,594 B1 | 1/2003 | Furukawa et al. | 372/36 |
| 6,747,736 B2 | 6/2004 | Takahashi | 356/319 |
| 6,771,677 B2 | 8/2004 | Furukawa et al. | 372/36 |
| 6,836,579 B2 | 12/2004 | Ouchi | 385/14 |
| 6,970,612 B2 | 11/2005 | Ouchi | 385/14 |
| 6,980,010 B2 | 12/2005 | Tonouchi et al. | 324/750 |
| 7,292,744 B2 | 11/2007 | Ouchi | 385/14 |
| 7,570,216 B2 | 8/2009 | Itsuji | 343/700 |
| 7,633,043 B2 * | 12/2009 | Ouchi | 250/214.1 |
| 2005/0215031 A1 | 9/2005 | Ouchi | 438/459 |
| 2005/0233490 A1 | 10/2005 | Kasai et al. | 438/46 |
| 2007/0070358 A1 | 3/2007 | Ouchi | 356/614 |
| 2007/0218376 A1 | 9/2007 | Ouchi | 430/56 |
| 2007/0280319 A1 | 12/2007 | Sekiguchi et al. | 372/45.01 |
| 2008/0217538 A1 | 9/2008 | Ouchi et al. | 250/338.4 |
| 2008/0314152 A1 | 12/2008 | Ouchi | 73/597 |
| 2009/0213880 A1 | 8/2009 | Ouchi et al. | 372/21 |

* cited by examiner

PHOTOCONDUCTIVE ELEMENT AND SENSOR DEVICE

CROSS REFERENCE TO RELATED APPLICATION

This application is a division of U.S. application Ser. No. 11/683,782, filed Mar. 8, 2007, the entire disclosure of which is incorporated by reference herein.

BACKGROUND OF THE INVENTION

1. Field of the Invention The present invention relates to a photoconductive element generating and detecting electromagnetic waves by the radiation of light and a method of manufacturing the same, and in particular, to a photoconductive element generating and detecting electromagnetic waves including at least a part of a frequency range of 30 GHz to 30 THz (hereinafter referred to as "terahertz wave") as frequency components by the radiation of light, a method of manufacturing the same, and a sensor device using the same.

2. Description of the Related Art

A non-destructive sensing technique using the terahertz wave has been developed in recent years. The electromagnetic wave in this frequency range finds its application in fields including an imaging technique for a safe fluoroscopic device substituting X rays, a spectroscopic technique in which absorption spectrum and complex dielectric constant inside a substance are determined to survey bonding state, a technique for analyzing biological molecules and a technique for evaluating carrier density and mobility.

A photoconductive element with an antenna serving also as an electrode provided on a photoconductive film with a thickness in the range of micrometers deposited on a substrate is suitably used as a terahertz wave generating unit (refer to Japanese Patent Application Laid-Open No. H10-104171. FIG. 7 illustrates an example of the configuration of the photoconductive element. A substrate 130 has, for example, a radiation-treated silicon-on-sapphire structure in which a silicon film as a photoconductive material is deposited on a sapphire substrate. In general, LT-GaAs grown on a GaAs substrate at low temperature is frequently used as a photoconductive film. A dipole antenna 138 formed on the surface includes a pair of dipole feeders 138a and 138b and a pair of dipole arms 139a and 139b. Optical pulses are focused in a gap 133. A voltage is applied across the gap to generate a terahertz wave pulse. If optical current is detected without the voltage applied across the gap, the terahertz wave pulse can be detected. A substrate lens 136 has a role to combine an electromagnetic wave from a slab mode (substrate mode) confined in the substrate 130 to a free-space radiation moment and to control the radiation angle of electromagnetic-wave propagation mode in space.

As shown in FIG. 7, passing through the substrate, a terahertz wave is generated, which is a typical configuration. Another configuration has been proposed in which a terahertz wave to be generated is taken out of the surface of a photoconductive film to prevent the wave from being dispersed and absorbed in the substrate (refer to Applied Physics Letters, vol. 85, p. 164, 2004).

The photoconductive film functioning to generate such a terahertz wave pulse is made only of a thin film formed on the substrate and the substrate has a role to hold the thin film. However, the substrate has the property of decreasing the transmittance of terahertz waves generated from the photoconductive film, decreasing efficiency in the generation of terahertz waves radiating from the other side of the substrate.

The proposal described in Applied Physics Letters, vol. 85, p. 164, 2004, which is of surface-generation type, has a configuration in which electromagnetic waves are reflected against incident laser beams, which complicates an optical locatement. In addition, the substrate has a confinement effect as a dielectric substance, for this reason, efficiency in the generation of electromagnetic waves on the surface cannot be practically increased so much.

A GaAs substrate is required when LT-GaAs is used as a photoconductive film. However, the substrate has a significant absorption due to optical phonon in the vicinity of a frequency of 7 THz. This lacks terahertz waves in the range of this absorption, causing a bottleneck in performing a terahertz-wave spectroscopy. The absorption is small in the surface-generation type disclosed in Applied Physics Letters, vol. 85, p. 164, 2004, however, it cannot be avoided.

SUMMARY OF THE INVENTION

The present invention is directed to a photoconductive element for generating and detecting electromagnetic waves comprising: a photoconductive film exhibiting conductivity by the radiation of light; a substrate holding the photoconductive film; and a thin film sandwiched between the photoconductive film and the substrate, the thin film being different in composition from the photoconductive film and the substrate; wherein the photoconductive film is provided with an antenna having a gap portion and an electrode electrically connectable to the antenna, and the substrate has an opening portion at least at a part where the gap portion of the antenna is located.

The thin film can include a material different from the substrate and the photoconductive film in etching rate for an etchant.

The thin film can be single crystal and has a strain structure different in lattice constant from at least one of the substrate and the photoconductive film.

In the photoconductive element, a material different from the substrate can be inserted into at least a part of the opening.

The side wall of the substrate forming the opening can have such a tapered shape that the opening portion gradually increases in size toward the outside of the element.

The element can be so adapted that the radiation of light into the gap portion generates and detects electromagnetic waves including at least a part of frequency range of 30 GHz to 30 THz as frequency components.

The opening can have a dimension larger than the wavelength of the electromagnetic waves to be generated or detected.

In the photoconductive element, an optical element converging the electromagnetic waves to be generated or detected can be fitted into the opening.

In the photoconductive element, a part of the photoconductive film where the gap portion of the antenna is located can be single crystal.

The present invention is directed to a method of manufacturing the photoconductive element comprising the steps of: forming a thin film different in composition from the photoconductive film and the substrate on the substrate; forming a photoconductive film on the thin film; forming the antenna having the gap portion on the photoconductive film; and etching the portion of the substrate corresponding to the portion of photoconductive film where the gap potion of the antenna is located from the side of the substrate opposite to the side where the gap portion exists so that the face of the thin film with a size larger than the wavelength of the electromagnetic wave is exposed.

The present invention is directed to a sensor device comprising the photoconductive element as at least one of an electromagnetic wave generating element and an electromagnetic wave detecting element, wherein electromagnetic waves generated by the electromagnetic wave generating element are caused to interact with a specimen, the interacting electromagnetic waves are detected by the electromagnetic wave detecting element, and a change is measured between the propagation state of the detected electromagnetic waves and the propagation state of electromagnetic waves detected by the electromagnetic wave detecting element when the specimen does not exist or the specimen changes, thereby acquiring information on the specimen.

The opening is formed by, for example, removing and thinning the substrate on the side of substrate, i.e., on the other side of the opening. Wherein, the antenna is a generic name for a portion where electromagnetic waves radiate or are combined and does not always refer to a specific shape. The gap refers to a distance between metallic parts and ranges for example from micrometers to millimeters.

In view of the above problems, the sensor device according to the present invention is provided with the above photoconductive element as at least one of the electromagnetic wave generating element and the electromagnetic wave detecting element. Electromagnetic waves from the electromagnetic wave generating element are caused to interact with a specimen to detect the electromagnetic waves subjected to the interaction by the electromagnetic wave detecting element to measure a change between the propagation state of the detected electromagnetic waves and that of the detected electromagnetic waves when a specimen does not exist or a specimen changes. This enables acquiring information on the physical properties of the specimen.

According to the present invention, the photoconductive element provided with the above opening allows generating and detecting broadband electromagnetic waves in the terahertz range in a comparatively high efficiency. For this reason, a comparatively high-sensitive spectral characteristic can be evaluated in a relatively wide frequency range, for example, by terahertz time-domain spectroscopy.

Further features of the present invention will become apparent from the following description of exemplary embodiments with reference to the attached drawings.

DESCRIPTION OF THE EMBODIMENTS

Figure 1A:
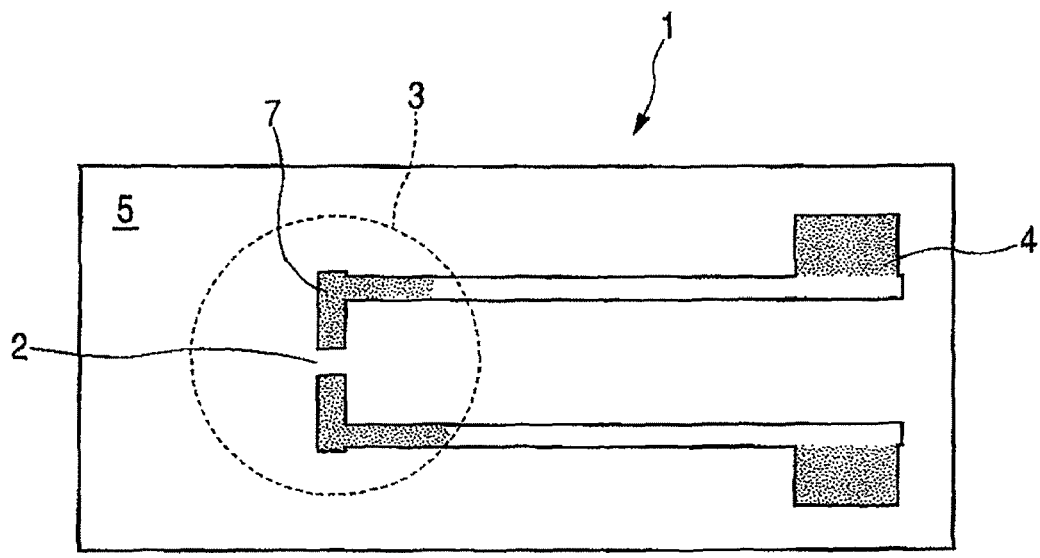
FIGS. 1A and 1B are a top view and a perspective view illustrating the photoconductive element according to a first embodiment of the present invention respectively.

The embodiment of the present invention is described below. In one embodiment of the present invention, an antenna which serves also as an electrode is prepared on the photoconductive film formed on the substrate and then the part of the substrate around the antenna is etched to remove it with only a part of the photoconductive film left to a size larger than the wavelength of generated or detected electromagnetic wave. An etching stop layer may be formed in advance on the substrate when the photoconductive film is formed on the substrate for the purpose of performing the above etching. The etching stop layer may be left as it is after the substrate has been removed or only one layer of photoconductive film may be left after a further removal. At this point, the substrate is not all removed but may be left thin-filmed. Such a configuration allows reducing or avoiding the influence of absorption peculiar to the substrate to enable providing a broadband terahertz time-domain spectroscopic instrument.

A resin (different from the substrate in material) small in absorption of electromagnetic waves may be embedded into at least a part of the hole (opening) of the substrate to reinforce the substrate. In addition, an optical element such as a ball lens low in refractive index to converge generated or detected electromagnetic waves is located in the hole made in the substrate or in a part of the hole into which a reinforced material is embedded, thereby decreasing reflection loss and improving NA (numerical aperture). Thus, a terahertz-wave use efficiency can be improved. The side wall of the opening formed in the substrate is tapered to gradually increase the size of the hole (opening) toward the outside of the element to form a horn-antenna shape, thereby improving efficiency in the collection and convergence of electromagnetic waves.

In the above photoconductive element, laser beams may be caused to be incident on any of the surfaces of the photoconductive film or the substrate where the hole is made. The use of the photoconductive element for both generation and detection of electromagnetic waves makes it effective to extend a measuring band in a terahertz time-domain spectroscopy.

EMBODIMENTS

Examples of embodiments are described in detail below.

First Embodiment

The first embodiment of the present invention is described with reference to FIGS. 1A and 1B. In a photoconductive element 1 according to the present invention, an epitaxial growth film 5 made of an AlAs layer (not shown) and a low temperature (LT) grown GaAs is formed on a semi-insulating (SI) GaAs substrate 6. An electrode 4 which serves also as a dipole antenna is formed on the surface of the LT-GaAs and about 5-μm gap portion 2 is located at the center of the antenna. Where, the AlAs layer is 0.1 μm in thickness and the LT-GaAs layer 5 is 2 μm in thickness. A dipole antenna formed in an antenna portion 7 is 30 μm in length. However, the numeric values and antenna shape are not limited to those stated herein. While a pair of the electrodes 4 and the antenna portion 7 are formed on the same plane as the epitaxial growth film 5 in the example illustrated in the figure, the epitaxial growth film may be interposed between a pair of the electrodes and the antenna portion to form a pair of the electrodes and the antenna portion on both the faces, providing the gap portion in the epitaxial growth film.

Figure 1B:
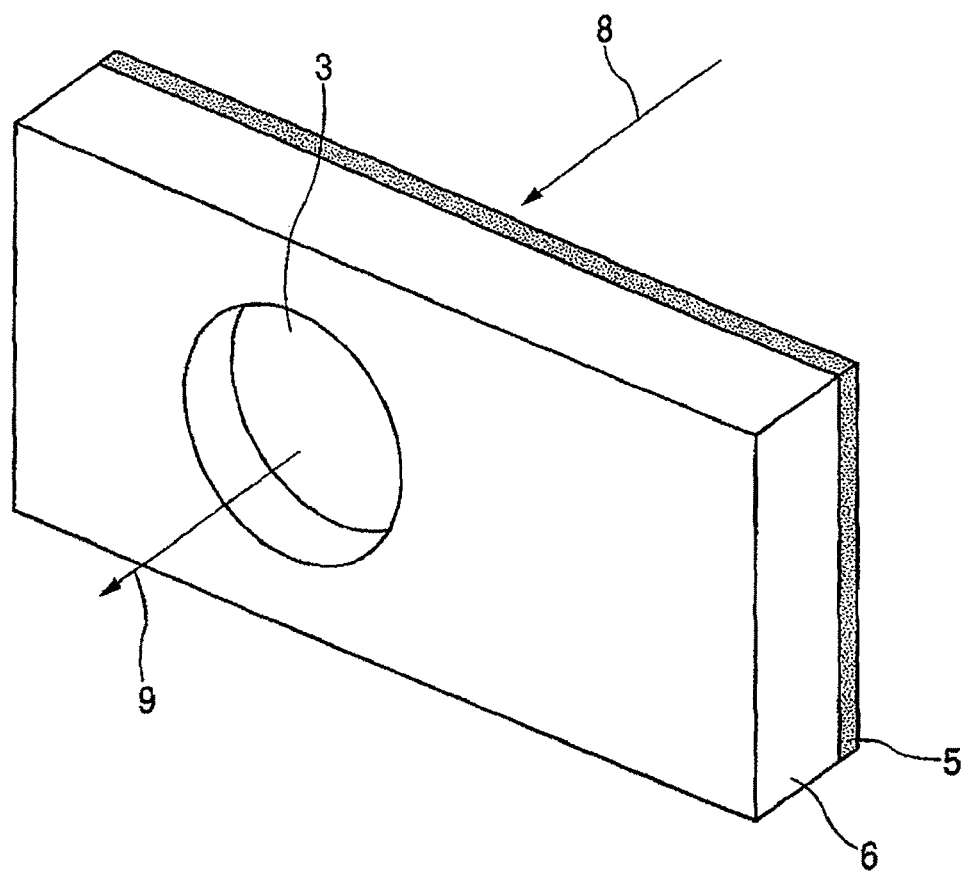

The portion of the GaAs substrate 6 on the other side of the area where the gap portion 2 and the antenna portion 7 are formed is hollowed out and removed to a diameter of about 5 mm to form an opening 3 illustrated in FIG. 1B. The opening 3 is formed by using both dry etching by reactive ion etching (RIE) using Gl₂ plasma and wet etching using mixed liquor of ammonia and hydrogen peroxide. The wet etchant can remove GaAs but slow in etching rate of AlAs, which is used to stop the etching at the AlAs layer. Thereafter, an etching stop layer AlAs is removed by hydrochloric acid. However, the etching stop layer may be left without removing. Thus, the thin film of the AlAs layer uses a material different in etching rate for a specific etchant from the substrate 6 and the photoconductive film of the LT-GaAs layer 5.

If such an etching stop layer does not exist, it is not easy to flatten the bottom face after etching has been performed to remove the substrate because the etching rate is different between the periphery and the center portion when hole etching is performed from the substrate side. The existence of the etching stop layer ensures that a flat and mirror plane surface is formed which does not exert influence such as scattering on terahertz waves. For this reason, the etching stop layer can be provided to remove the substrate to such an extent that the etching stop layer is reached.

The use of the configuration reduces or prevents the absorption of terahertz waves into a conventional GaAs substrate to improve efficiency in the generation of electromagnetic waves. At the same time, a strong absorption due to phonon in the vicinity of a frequency of 7 THz disappears, so that the radiation of a laser beam 8 allows a broadband terahertz pulse 9 to be generated in the transmission-type locatement illustrated in FIG. 1B. Furthermore, a broadband terahertz light can be detected.

At this point, the AlAs layer as the etching stop layer has turned into a layer higher in crystallinity than the LT-GaAs. For this reason, the influence of damage of the GaAs substrate surface on the LT-GaAs is reduced as compared with cases where the AlAs layer does not exist, bringing the advantage of increasing efficiency in the generation and detection of terahertz waves.

On the other hand, if the etching stop layer does not exist, there can be a method in which a hole is made in advance on the other side of the substrate, the hole is filled up with a material except a single crystal, the surface is polished again and the LT-GaAs layer is deposited thereon. However, in the above method, the LT-GaAs layer is deposited on a non-single crystal layer, so that the LT-GaAs film is turned polycrystal or amorphous, which makes it difficult to increase efficiency in the generation of electromagnetic waves. In this respect, if the above typical etching stop layer is provided, the LT-GaAs layer can be single crystal in the vicinity of the gap portion of the antenna in the area where the hole is made. In general, the single crystal is defined as something which the same molecular groups are three-dimensionally located with a certain constant regularity in a solid within a specified range. In the photoconductive element of the present invention, the LT-GaAs layer is single crystal at least in the vicinity of the gap portion 2 formed at the antenna portion 7 to increase efficiency in the generation of electromagnetic waves. Furthermore, a strain resulting from a slight difference in lattice constant between the AlAs layer and the GaAs layer is expected to improve characteristics. In other words, when the substrate 6 is removed with the single crystal AlAs layer larger in lattice constant than the GaAs substrate left, a pseudocrystal AlAs film exhibits an intrinsic lattice constant to attract strain by the LT-GaAs layer 5 of the photoconductive film thereon, resultantly improving the mobility of carriers in the LT-GaAs layer to improve characteristics such as efficiency in the generation and detection of electromagnetic waves.

Figure 3:
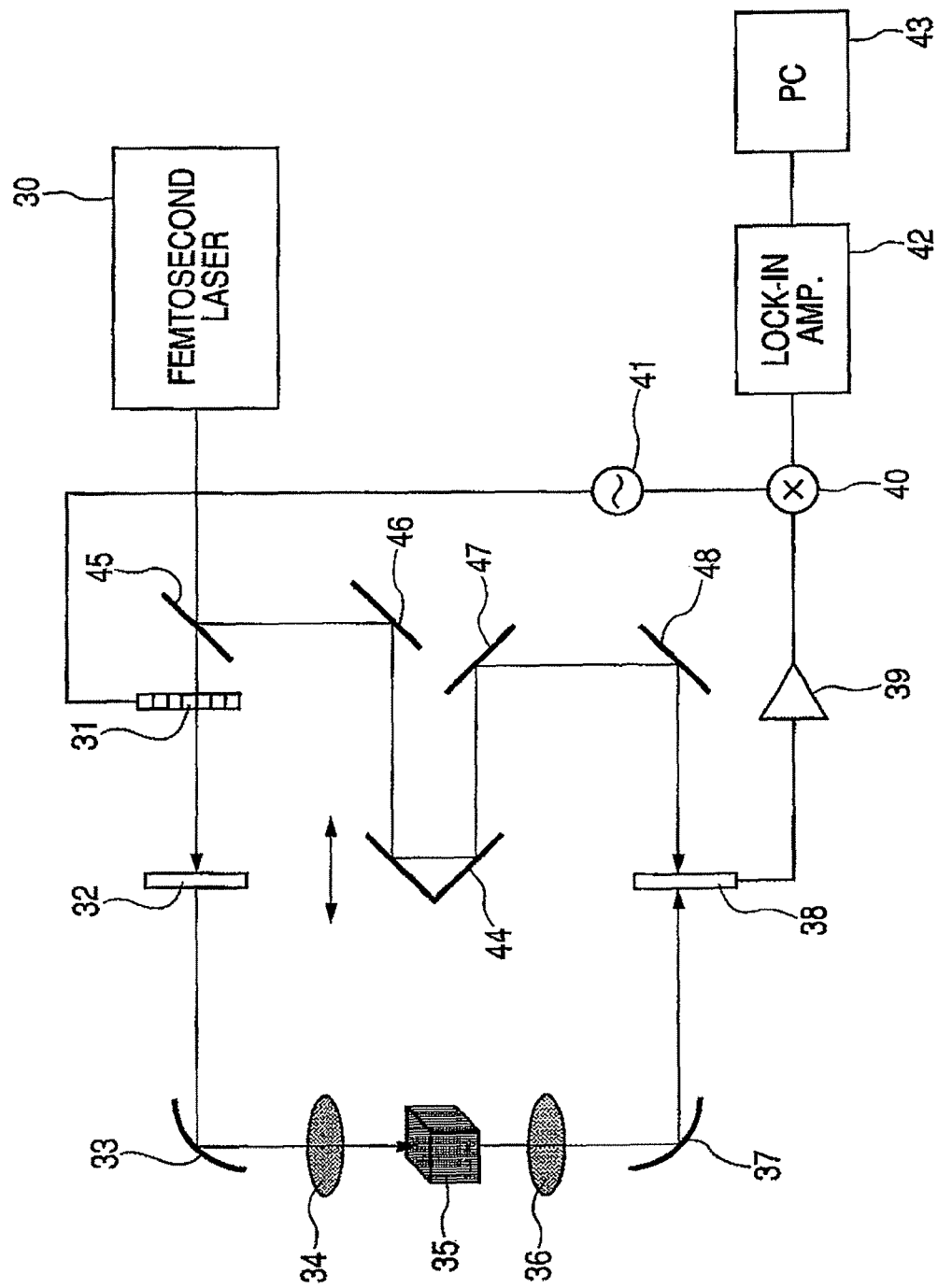
FIG. 3 is a diagram describing a terahertz measuring system using the photoconductive element according to the present invention.

FIG. 3 illustrates the configuration of the terahertz time-domain spectroscopic instrument (THz-TDS) using the above substrate-removed photoconductive element. In the configuration, a photoconductive element (electromagnetic wave generating element) 32 according to the present embodiment is radiated with light with a wavelength of 800 nm from a laser 30 generating a 10-femtosecond ultrashort pulse through a chopper 31. A 10-V voltage is applied across the gap of the antenna portion to cause the photoconductive element 32 to generate terahertz waves. The terahertz wave passes through a parabolic mirror 33 and a lens 34 to be properly converged and be incident on a specimen 35. The terahertz wave transmitted through the specimen 35 is similarly incident on a photoconductive element (electromagnetic wave generating element) 38 through a lens 36 and a parabolic mirror 37.

The face on the other side of the photoconductive element 38 is radiated with light beams from the femtosecond laser 30 branched by mirrors 45 to 48. Terahertz waveforms are observed while a delay time is being varied with a delay optical system 44. The above is similar to an ordinary THz-TDS instrument and the others are also similar to an ordinary THz-TDS instrument. Signals are processed in a lock-in amplifier 42 and PC 43 through an amplifier 39. That is to say, resolution data of intensity of the pulse electromagnetic wave transmitted through the specimen 35 in each delay time is sequentially stored as time-series data and Fourier transformed by the PC 43 to be transformed into frequency space. Thus, the intensity amplitude and the optical spectrum of phase of the pulse electromagnetic wave transmitted through the specimen 35 are obtained. Incidentally, reference numeral 40 is a mixer and 41 is an oscillator. In the above system, when the specimen 35 does not exist, Fourier spectra which gradually decrease to at least about 10 THz without absorption at 7 THz are obtained, which permits the measurement of the complex dielectric constant of the specimen 35 in a broad band without the lack of a frequency band.

Using this sensor, electromagnetic waves generated by the electromagnetic wave generating element are caused to interact with the specimen and the interacting electromagnetic waves are detected by the electromagnetic wave detecting element. A change can be measured between the propagation state of the detected electromagnetic waves and that of the detected electromagnetic waves when the specimen does not exist or a specimen changes. Such a measurement enables acquiring information on the physical properties of the specimen.

As described above, the THz-TDS instrument illustrated in FIG. 3 is capable of measuring signals including those around 7 THz by using the photoconductive element according to the present embodiment both for generation and for detection. Needless to say, the photoconductive element according to the present embodiment may be used for only one of generation and detection.

As stated above, in the photoconductive element according to the present embodiment, the opening 3 is formed in a part of the substrate 6 holding the photoconductive film 5 (or a part corresponding to the area where the gap portion 2 of the antenna portion 7 is located), as illustrated in FIGS. 1A and 1B, to prevent the GaAs substrate 6 from absorbing terahertz waves due to an optical phonon. This realizes the element capable of generating and detecting terahertz waves at a comparatively high efficiency and at a broad band. For this reason, in the forgoing terahertz time-domain spectroscopy, spectral characteristics can be evaluated in a relatively high sensitivity and in a comparatively broad frequency range.

Figure 2A:
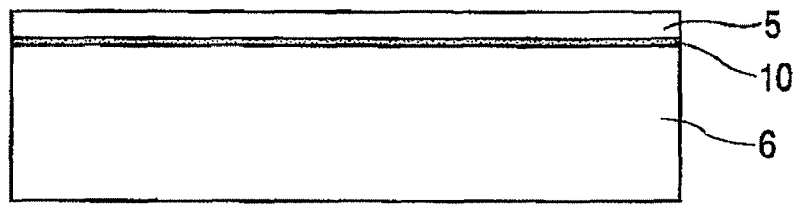
FIGS. 2A, 2B, 2C and 2D are process charts describing an example of the method of producing the photoconductive element according to the first embodiment of the present invention.

An example of a process for producing the photoconductive element is described below with reference to FIG. 2A to 2D. In FIG. 2A, an AlAs etching stop layer 10 and the LT-GaAs film 5 are epitaxially grown on the SI—GaAS substrate 6 by molecular beam epitaxy (MBE). A graded layer gradually varying in Al composition may be provided on an interface between the two layers if needed. All the epitaxial layers are not doped and have the thickness described above. The above process is a first step in which the LT-GaAs photoconductive film 5 and the thin film of the AlAs etching stop layer 10 different in composition from the substrate 10 are formed on the substrate 6 and a second step in which the LT-GaAs photoconductive film 5 is formed on the surface of the thin film of the AlAs etching stop layer 10.

Figure 2B:
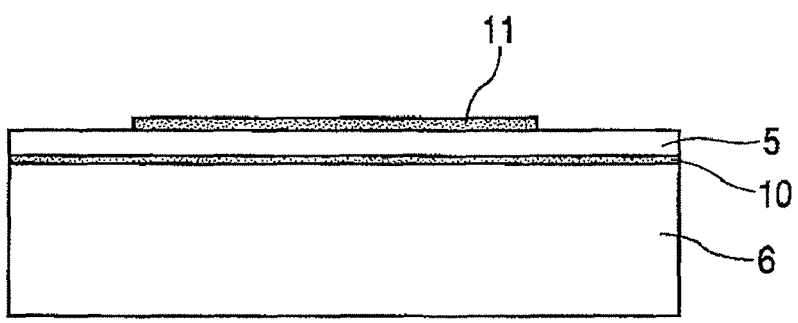
Figure 2C:
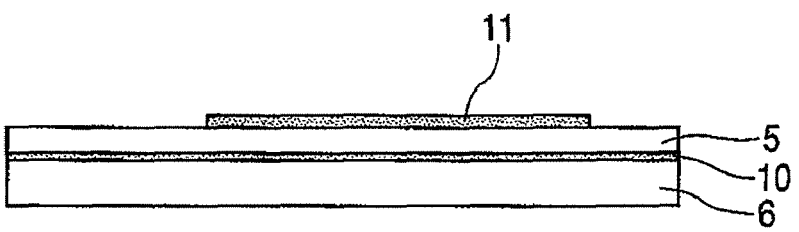

In FIG. 2B, an antenna 11 serving also as an electrode including AuGe, Ni and Au is formed on the surface of the LT-GaAs film 5 by a lift-off process and annealed at a temperature of 400° C. to improve contact. The surface pattern is shown in FIGS. 1A and 1B. This process is a third step in which the antenna 7 with the gap portion 2 is formed on the surface of the LT-GaAs film 5. After that, in FIG. 2C, the substrate 6 is thinned to a thickness of about 100 μm by polishing.

Figure 2D:
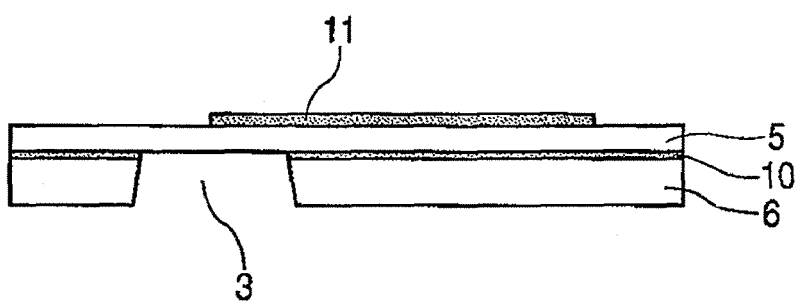

In addition, in FIG. 2D, a part of the substrate 6 to be etched is subjected to a 5-mm diameter hole pattering (not shown) with photolithography using a double sided aligner and dry-etched to about 90 μm using the RIE mentioned earlier. Furthermore, the other 10-μm portion is wet-etched by the above etchant. This enables a 5-mm circular hole (opening) 3 to be formed. The above process is a fourth step in which a part with a diameter of 100 μm or more of the substrate 6 is etched on the side of substrate, i.e., on the other side of the opening to such an extent that the face of the thin film 10 is exposed, in the part of the substrate 6 corresponding to the part of the photoconductive film 5 where the gap potion of the antenna is located. The opening portion 3 may be larger in dimension than the wavelength of electromagnetic wave to be generated or detected, so that diameter can be properly designed according to the wavelength of a targeted electromagnetic wave. In the present embodiment, the substrate 6 can be etched to such an extent that the thin film of the AlAs etching stop layer 10 is exposed, however, the 10-μm thinned substrate portion may be left without wet etching.

In addition, the etching conditions are controlled when the substrate is etched to cause the side wall to be tapered outwardly, thereby causing the antenna to function as a horn antenna (FIG. 2D illustrates the outwardly tapered hole 3). The thickness of a resist mask for etching may be tapered to control an etching depth depending on places to form the taper shape of the side wall. The formation of such a horn antenna causes the space combination of terahertz waves to be generated and detected to have directivity, allowing the improvement of efficiency in the collection and convergence of terahertz waves. Metal such as Au or Al may be coated on the side wall to improve a reflection coefficient.

Second Embodiment

Figure 4:
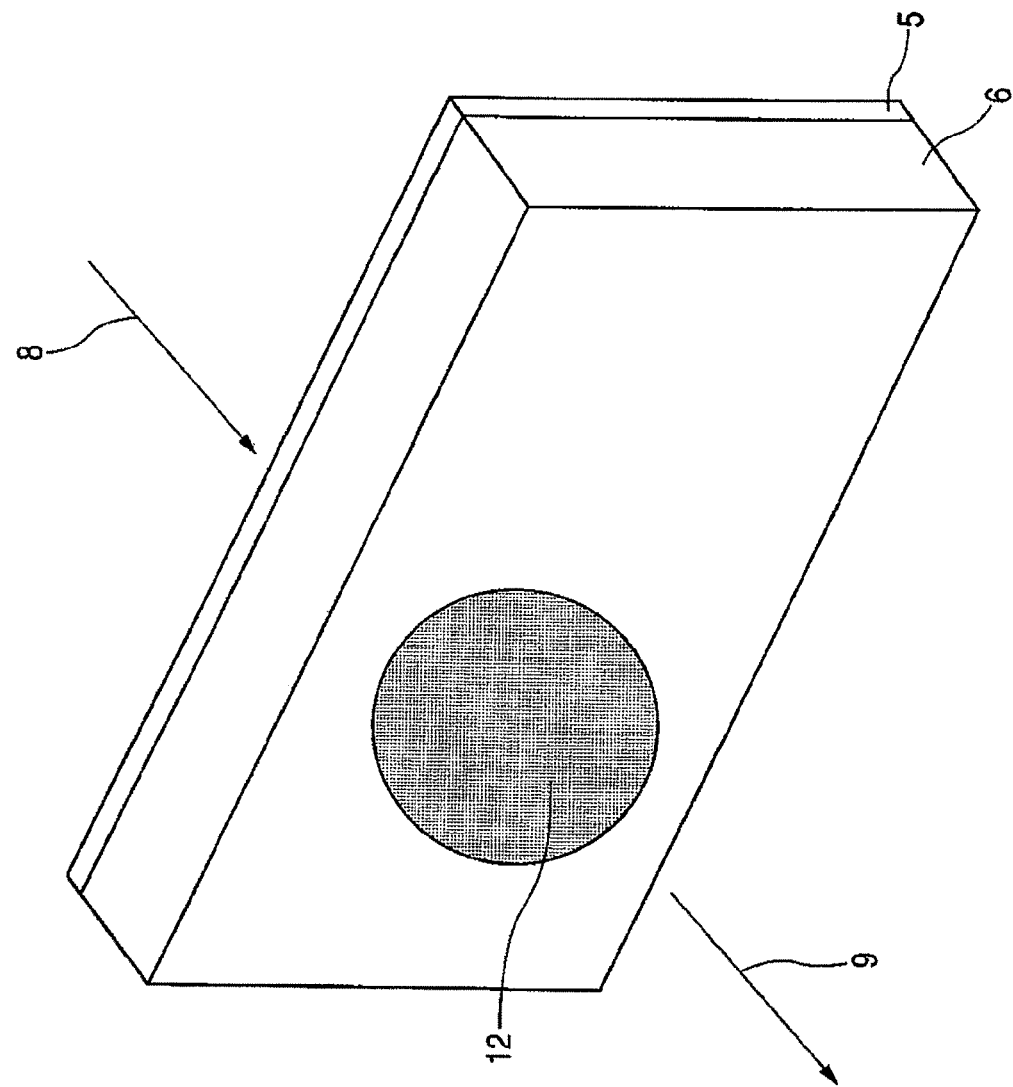
FIG. 4 is a perspective view of a photoconductive element of a second embodiment according to the present invention.

The second embodiment according to the present invention is described below. FIG. 4 illustrates the second embodiment. The substrate 6 and the epitaxial layer 5 in FIG. 4 are the same as those in the first embodiment in configuration. In the present embodiment, a spherical, hemispheric or aspherical lens 12 is fitted into a hole (opening) made by removing the substrate to converge terahertz waves. Resin such as polyethylene, polyolefin or Teflon (trade name) or quartz may be used as a material for the lens. Hitherto, the existence of the substrate causes reflection due to a refractive index difference (for example, a difference between a refractive index of 3.5 of the substrate and a refractive index of 1.5 of a low refractive index material), so that it has been difficult to use a low refractive index material. However, the removal of the substrate allows a lens of a low refractive index material to be located in the vicinity of an electrode of a terahertz wave generating source. Thus, the advantage can be fully used that a low refractive index material is low in reflection loss. Adhesive such as epoxy resin may be used to fix the lens 12.

In the present embodiment, an optical element such as the lens 12 for converging electromagnetic waves to be generated or detected is fitted into an opening, further improving efficiency in the use of terahertz waves and S/N of the THz-TDS instrument.

Third Embodiment

Figure 5:
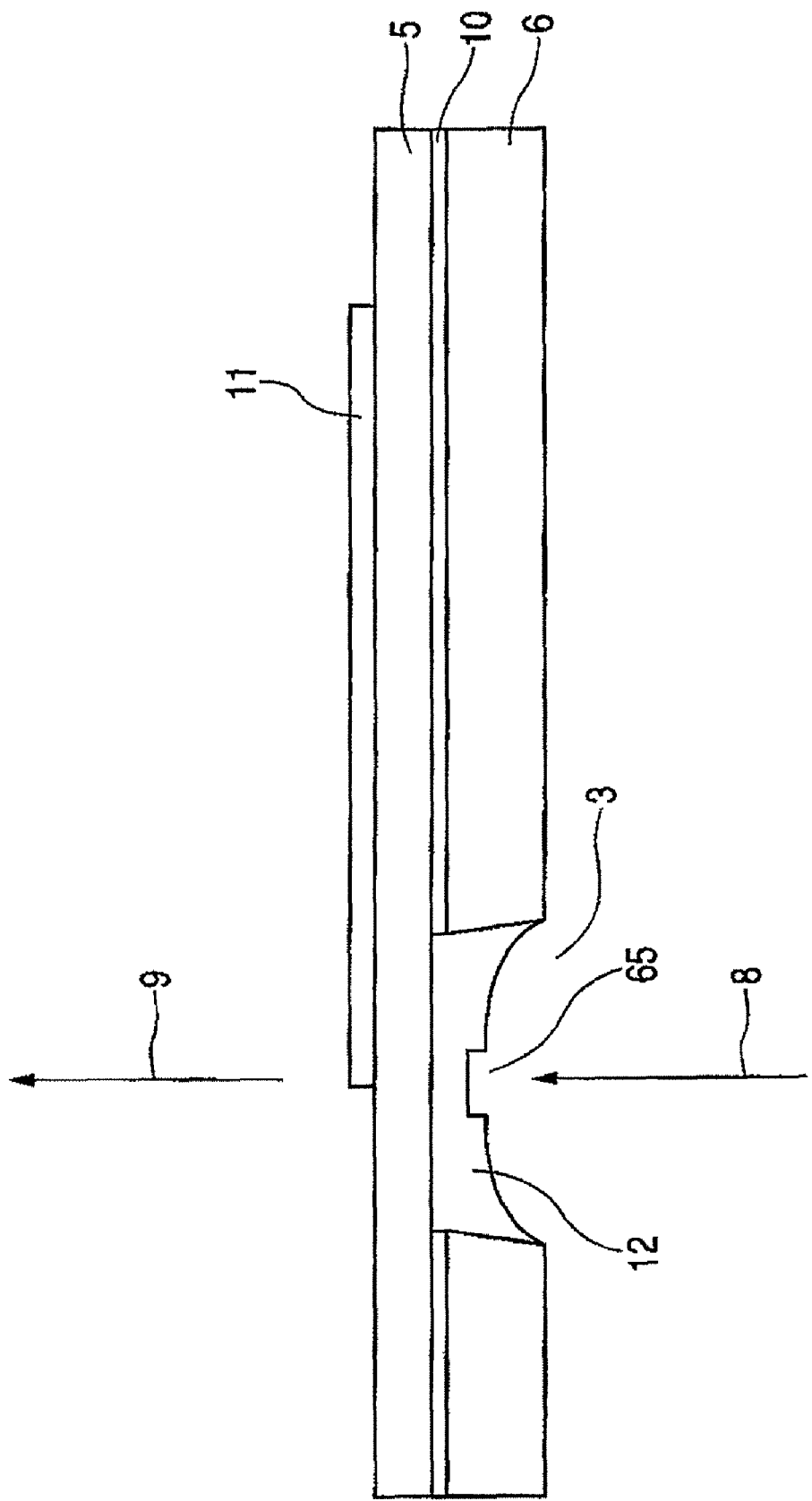
FIG. 5 is a cross section of a photoconductive element of a third embodiment according to the present invention.

FIG. 5 illustrates the third embodiment according to the present invention. In FIG. 5, the substrate 6, the etching stop layer 10, the photoconductive film 5 and the antenna 7 are the same in configuration as those in the above embodiments, so that description thereof is omitted. In the present embodiment, a material 64 with an appropriate thickness such as resin which less absorbs terahertz waves and light is embedded into a hole (opening) made by removing the substrate to reinforce a thinned photoconductive film 62.

Resin such as polyimide, polyethylene, SU-8 and BCB can be used as a material 64 for embedding the hole 3 (opening) of the substrate 6. A dip portion 65 may be provided on the resin 64 used for embedding the hole by photolithography and RIE to be located to the center of an antenna gap (gap portion) formed on the surface of the LT-GaAs layer. This realizes a configuration in which the laser beam is incident from the side of the substrate 60, contrary to the above embodiment, to generate terahertz waves from the surface of the LT-GaAs layer. This allows the dip portion 65 to be taken as an alignment target of the laser beam to further reduce the absorption of terahertz waves into the resin 64.

In the present embodiment in which the thinned photoconductive film 62 is reinforced, the opening of the substrate 6 is allowed to be further increased to 1 cm in diameter. This enables terahertz waves with a wide range to be spatially taken out without repellence by the wall face of opening of the substrate 6.

Figure 6:
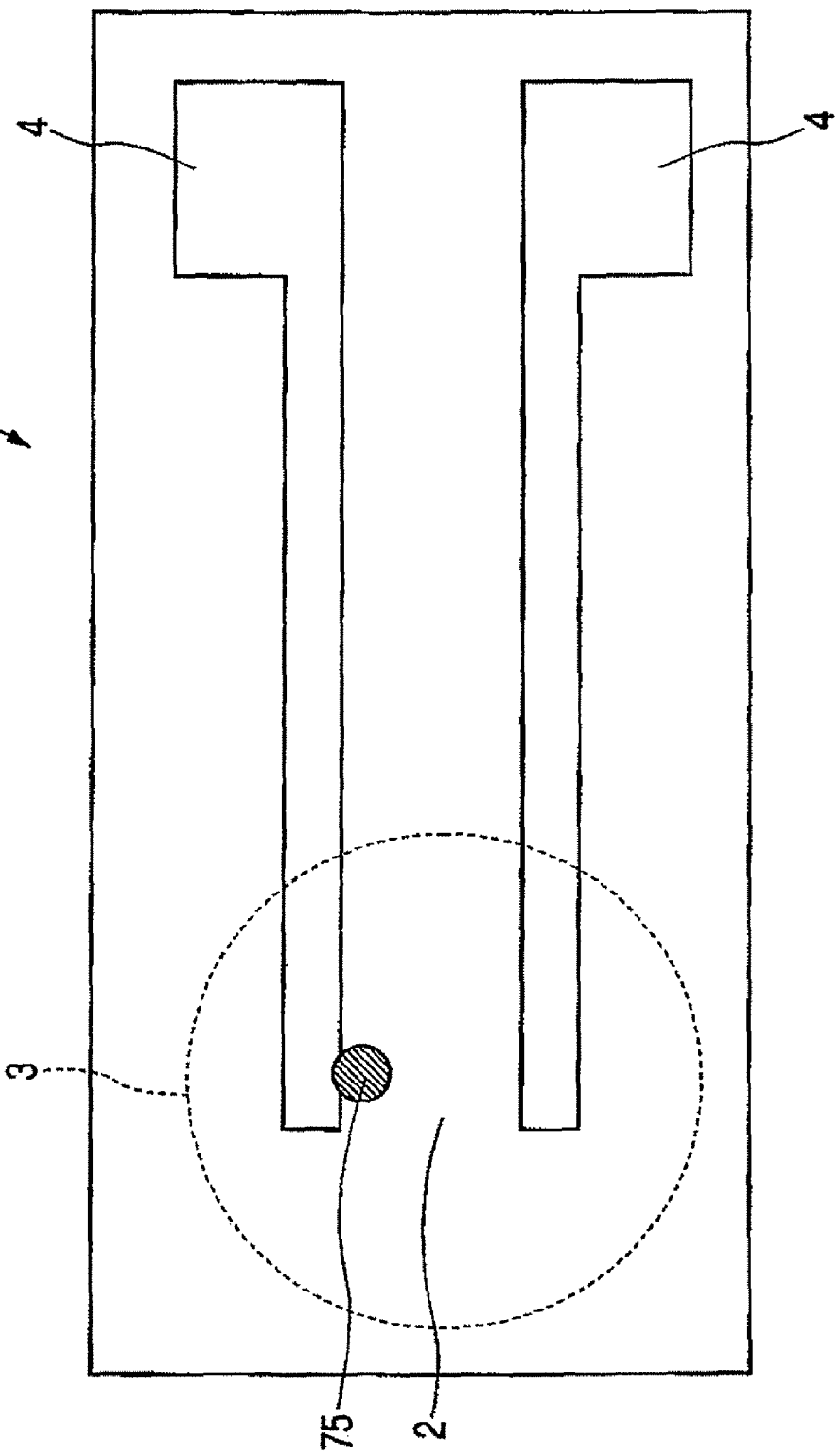
FIG. 6 is a diagram describing another antenna configuration in the present invention.
Figure 7:
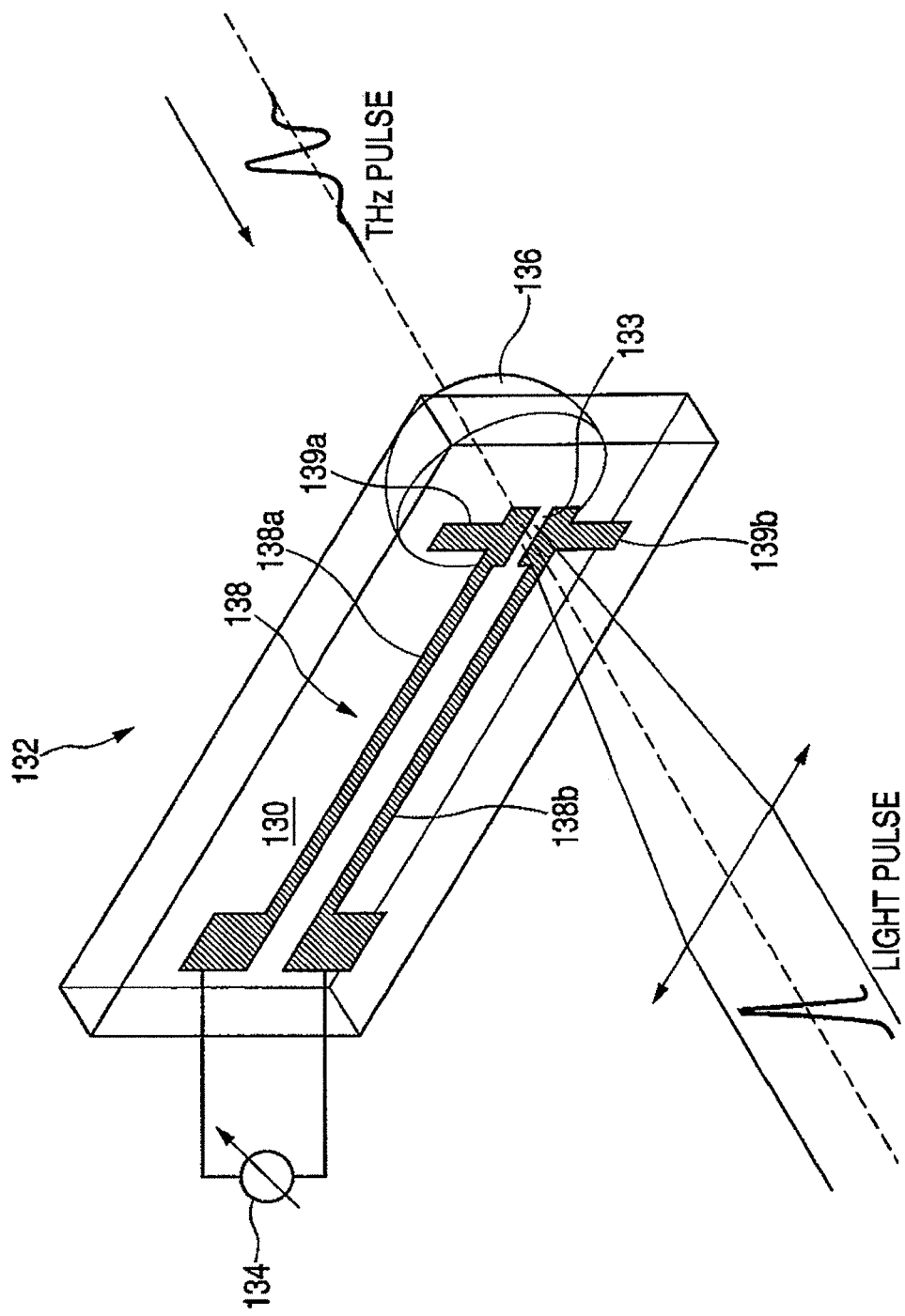
FIG. 7 is a perspective view illustrating an example of a conventional terahertz generating section.

In the present embodiment, a circle is taken as an example of the opening in the substrate and described, however, other shapes such as a square, rectangle or ellipse may be used. In addition, for the antenna, various types of antennas such as a bow tie, slot and spiral may be used instead of the dipole antenna. Furthermore, as illustrated in FIG. 6, a photoconductive element 71 may be formed in which a gap portion (opening) between two electrodes 4 is set to 50 μm to 500 μm and the area around any one of the electrodes 4 is radiated with light, instead of a definite shape of an antenna.

The following materials can be used as the photoconductive film as well as GaAs: compound semiconductor (for example, InGaAs, InGaSb, InAs and InN) which are selected from Al, Ga and In as III group elements and N, P, As and Sb as V group elements; semiconductor including IV group elements such as Si and Ge; and II-VI group elements such as ZnSe. Those materials can be applied as long as they are photoconductive.

In the above embodiment, a description is made of the system using a femtosecond laser as an excitation light source for THz-TDS measurement. However, the following well-known method is available as another method. A difference between oscillating frequencies of two stable CW oscillation light sources is tuned to a desired terahertz band to radiate the photoconductive element with the oscillating light to generate continuous terahertz waves corresponding to the beat frequencies of the oscillating frequencies, thereby performing a terahertz wave spectral measurement. In this case, the variation of the beat frequencies allows a spectral measurement.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2006-073613, filed Mar. 17, 2006, and No. 2006-342883 filed Dec. 20, 2006, which are hereby incorporated by reference herein in their entirety.

What is claimed is:

1. A photoconductive element for generating and detecting electromagnetic waves, comprising:
    a photoconductive film that exhibits conductivity from radiation of light;
    a substrate holding the photoconductive film; and
    a thin film sandwiched between the photoconductive film and the substrate, the thin film including a material different from the substrate and the photoconductive film in etching rate by an etchant,
    wherein the photoconductive film is provided with an antenna having a gap portion and an electrode electrically connectable to the antenna, and
    wherein the substrate has an opening portion at least at a part where the gap portion of the antenna is located.

2. The photoconductive element according to claim 1, wherein the electromagnetic wave is a terahertz wave.

3. The photoconductive element according to claim 1, wherein the etching rate of the substrate by the etchant is higher than the etching rate of the material included in the thin film by the etchant.

* * * * *